(12) United States Patent
Xiao et al.

(10) Patent No.: US 11,273,061 B2
(45) Date of Patent: Mar. 15, 2022

(54) COVERED STENT

(71) Applicant: LIFETECH SCIENTIFIC (SHENZHEN) CO., LTD, Shenzhen (CN)

(72) Inventors: Benhao Xiao, Shenzhen (CN); Liming He, Shenzhen (CN); Caiping Liu, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 212 days.

(21) Appl. No.: 16/473,359

(22) PCT Filed: Dec. 19, 2017

(86) PCT No.: PCT/CN2017/117298
§ 371 (c)(1),
(2) Date: Mar. 4, 2020

(87) PCT Pub. No.: WO2018/121364
PCT Pub. Date: Jul. 5, 2018

(65) Prior Publication Data
US 2020/0352752 A1 Nov. 12, 2020

(30) Foreign Application Priority Data
Dec. 28, 2016 (CN) .......................... 201611238491.9

(51) Int. Cl.
*A61F 2/86* (2013.01)
(52) U.S. Cl.
CPC ........ *A61F 2/86* (2013.01); *A61F 2210/0014* (2013.01); *A61F 2240/001* (2013.01)

(58) Field of Classification Search
CPC .................................... A61F 2/06; A61F 2/82
See application file for complete search history.

(56) References Cited

U.S. PATENT DOCUMENTS

| 10,548,709 | B2 * | 2/2020 | Wang ........................ A61F 2/07 |
| 2003/0018378 | A1 | 1/2003 | Sarac |

(Continued)

FOREIGN PATENT DOCUMENTS

| CN | 101627933 A | 1/2010 |
| CN | 101703812 A | 5/2010 |

(Continued)

OTHER PUBLICATIONS

International Search Report dated Mar. 21, 2018 in corresponding International application No. PCT/CN2017/117298; 10 pages.

(Continued)

*Primary Examiner* — Yashita Sharma
(74) *Attorney, Agent, or Firm* — Maier & Maier, PLLC

(57) ABSTRACT

A covered stent, including a proximal end end surface, a distal end end surface and a peripheral surface located between the proximal end end surface and the distal end end surface, the peripheral surface including an inner surface and an outer surface. The outer surface is covered with a first coating membrane, and the inner surface is covered with a second coating membrane. The covered stent further includes a stent main body, which is between the first coating membrane and the second coating membrane. At least one of two ends of the first coating membrane and the second coating membrane fold inward or outward so as to wrap at least one from among the proximal end end surface and the distal end end surface.

4 Claims, 4 Drawing Sheets

(56) References Cited

U.S. PATENT DOCUMENTS

| | | |
|---|---|---|
| 2004/0102855 A1 | 5/2004 | Shank |
| 2005/0113903 A1 | 5/2005 | Rosenthal et al. |
| 2007/0135906 A1 | 6/2007 | Badylak et al. |
| 2013/0184808 A1 | 7/2013 | Hall et al. |

FOREIGN PATENT DOCUMENTS

| | | |
|---|---|---|
| CN | 101945623 A | 1/2011 |
| CN | 102292053 A | 12/2011 |
| CN | 103720529 A | 4/2014 |
| CN | 104027152 A | 9/2014 |
| CN | 205041567 U | 2/2016 |
| EP | 1 704 835 A2 | 9/2006 |
| JP | 4494144 B2 | 6/2010 |
| WO | 2017125312 A1 | 7/2017 |

OTHER PUBLICATIONS

Indian Office Action dated Mar. 17, 2021, in connection with corresponding IN Application No. 201917029077 (5pp.).

* cited by examiner

A-A

COVERED STENT

FIELD

The present application relates to the field of implantable medical devices, and more particularly relates to a covered stent.

BACKGROUND

An existing covered stent generally adopts a single-layer coating membrane structure or a two-layer coating membrane structure. After a stent having the single-layer coating membrane structure is implanted into a body, a metal stent would be exposed to blood and may be corroded after long time. The single-layer coating membrane structure is directly adhered and sealed to the inner wall of a blood vessel by the metal stent, causing low sealing property and low biocompatibility.

In the two-layer coating membrane structure, both the inner and outer surfaces of the metal stent are covered with membranes, and inner and outer coating membranes and the metal stent are combined into a whole by high-temperature thermal treatment. After this two-layer coating membrane structure is implanted into the body, the metal stent avoids being directly exposed to the blood to prevent corrosion of the metal stent and release of metal ions; and furthermore, the proximal end of the stent is directly adhered to the inner wall of the blood vessel by the coating membranes, achieving relatively high sealing property and high biocompatibility.

However, in the two-layer coating membrane structure, the inner and outer coating membranes are combined into a whole by the thermal treatment method, and thus may be torn under long-term impact of the blood on the proximal-end end surface and the distal-end end surface of the covered stent to further cause the exposure of the metal stent to the blood, which accelerates the corrosion of the metal stent to release the metal ions. Particularly, nickel ions released by a metal stent made of a nickel-titanium alloy in the blood have a carcinogenic effect. In addition, tear openings formed by the tearing of the inner and outer coating membranes on the proximal-end end surface and the distal-end end surface of the covered stent would slow down the blood flow to easily cause thrombosis in the tearing openings, and may increase the impact force of the flowing blood to the covered stent, thereby increasing the risk of stent displacement.

SUMMARY

The present application provides a covered stent capable of avoiding inner and outer coating membranes on the proximal-end end surface and the distal-end end surface from being torn so as to overcome the defects in the prior art.

One technical solution of the present application adopted to solve the technical problem is as follows: a covered stent, having a proximal-end end surface, a distal-end end surface and a peripheral surface located between the proximal-end end surface and the distal-end end surface. The peripheral surface includes an inner surface and an outer surface opposite to the inner surface. The outer surface is covered with a first coating membrane, and the inner surface is covered with a second coating membrane. The covered stent further includes a stent main body arranged between the first coating membrane and the second coating membrane. At least one of two ends of the first coating membrane and the second coating membrane are folded inwards or outwards so as to cover at least one of the proximal-end end surface and the distal-end end surface.

In one embodiment of the present application, the two ends of the first coating membrane and the second coating membrane are folded towards the inner surface and are connected with the second coating membrane through the stent main body.

In one embodiment of the present application, the two ends of the first coating membrane and the second coating membrane are folded towards the outer surface and are connected with the first coating membrane through the stent main body.

In one embodiment of the present application, the two ends of the second coating membrane are folded towards the outer surface and are connected with the second coating membrane through the stent main body, and the two ends of the first coating membrane are folded towards the inner surface and are connected with the second coating membrane.

The present application further solves the technical problems as follows: a membrane covering method of the above-mentioned covered stent is provided, including:

S1, covering the outer surface of the covered stent with a first coating membrane, and covering the inner surface with a second coating membrane;

S2, thermally treating the covered stent covered with the coating membranes so as to adhere the first coating membrane and the second coating membrane;

S3, after the coating membranes are cooled, cutting two ends of the first coating membrane and the second coating membrane to required lengths;

S4, folding the two ends of the first coating membrane and the second coating membrane towards the inner surface; and S5, thermally treating the first coating membrane and the second coating membrane which are folded towards the inner surface so as to adhere the folded coating membranes with the second coating membrane.

Another technical solution that the present application provides is as follows: a membrane covering method of the above-mentioned covered stent is provided, including:

S1, covering the outer surface of the covered stent with a first coating membrane, and covering the inner surface with a second coating membrane;

S2, thermally treating the covered stent covered with the coating membranes so as to adhere the first coating membrane and the second coating membrane;

S3, after the coating membranes are cooled, cutting two ends of the first coating membrane and the second coating membrane to required lengths;

S4, folding the two ends of the first coating membrane and the second coating membrane towards the outer surface; and S5, thermally treating the first coating membrane and the second coating membrane which are folded towards the outer surface so as to adhere the folded coating membranes with the first coating membrane.

Another technical solution that the present application provides is as follows: a membrane covering method of the above-mentioned covered stent is provided, including:

S1, covering the inner surface with a second coating membrane, and cutting two ends of the second coating membrane to required lengths;

S2, folding the two ends of the second coating membrane towards the outer surface;

S3, thermally treating the covered stent in Step S2 so as to allow the two ends of the second coating membrane to be adhered with the second coating membrane through a stent main body;

S4, covering the outer surface with a first coating membrane, and cutting two ends of the first coating membrane to required lengths;

S5, folding the two ends of the first coating membrane towards the inner surface; and S6, thermally treating the covered stent in Step S5 so as to allow the two ends of the first coating membrane to be adhered with the second coating membrane.

The prevent application may prevent blood flow from directly impacting the coating membranes on the inner and outer surfaces of the proximal-end end surface and/or the distal-end end surface through a flanging design for the coating membranes on the proximal-end end surface and/or the distal-end end surface of the covered stent, thereby avoiding tearing of the coating membranes of the inner and outer surfaces caused by long-term blood flow impact and a series of adverse effects caused by the tearing of the coating membranes.

BRIEF DESCRIPTION OF THE DRAWINGS

The present application will be further described below in combination with accompanying drawings and embodiments. In the drawings.

DETAILED DESCRIPTION

To understand the technical features, objectives and effects of the present application more clearly, specific implementation modes of the present application are now described in detail in contrast with the accompanying drawings.

First Embodiment

Figure 1:
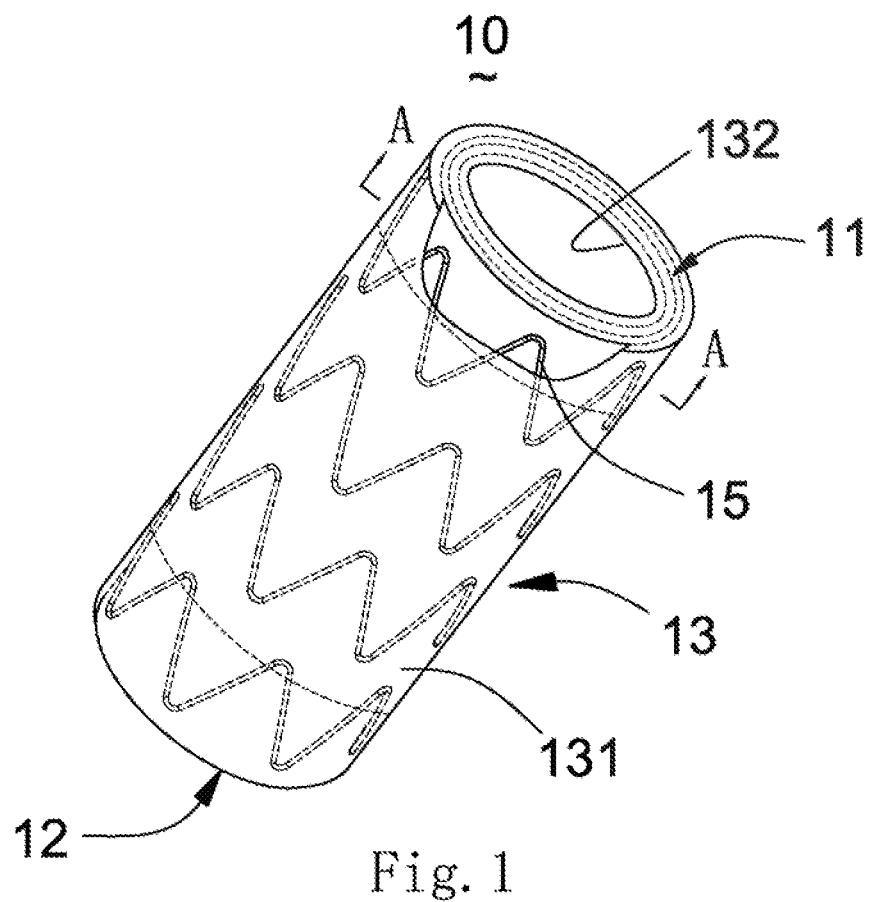
FIG. 1 is a structural schematic diagram of a first embodiment of a covered stent of the present application.

As shown in FIG. 1, a covered stent 10 is a tubular structure (used for forming a blood flow channel) with openings at two ends, and has a proximal-end end surface 11, a distal-end end surface 12 and a peripheral surface 13 located between the proximal-end end surface 11 and the distal-end end surface 12. The peripheral surface 13 includes an outer surface 131 and an inner surface 132 opposite to the outer surface 131. The outer surface 131 and the inner surface 132 are respectively located on two sides of a stent main body 15. In the present embodiment, the outer surface 131 is covered with a first coating membrane 141, and the inner surface 132 is covered with a second coating membrane 142. The first coating membrane 141 and the second coating membrane 142 have certain thicknesses and are generally made of a biocompatible macromolecular material, such as a PET (polyethylene terephthalate) membrane or PTFE (poly tetra fluoroethylene) membrane. The stent main body 15 is arranged between the first coating membrane 141 and the second coating membrane 142. The first coating membrane 141 and the second coating membrane 142 are adhered by thermal treatment so as to clamp the stent main body 15 therebetween. The stent main body 15 is cut and expanded from a biocompatible plastic expansion material tubular product known in the art, and the tubular product may be medical stainless steel, or a cobalt-nobelium alloy, or a self-expansion material such as a nickel-titanium alloy. When made of a plastic expansion material, the stent main body 15 may be radially compressed in a delivery sheath tube and may be expanded to an initial shape and size through an inflatable balloon or an equivalent expansion mechanism. When made of the self-expansion material, the stent main body 15 may be radially compressed in the delivery sheath tube and recovers the initial shape and size in the absence of the compression of the delivery sheath tube. The stent main body 15 may be cut from the tube product or woven by a metal wire.

Figure 2:
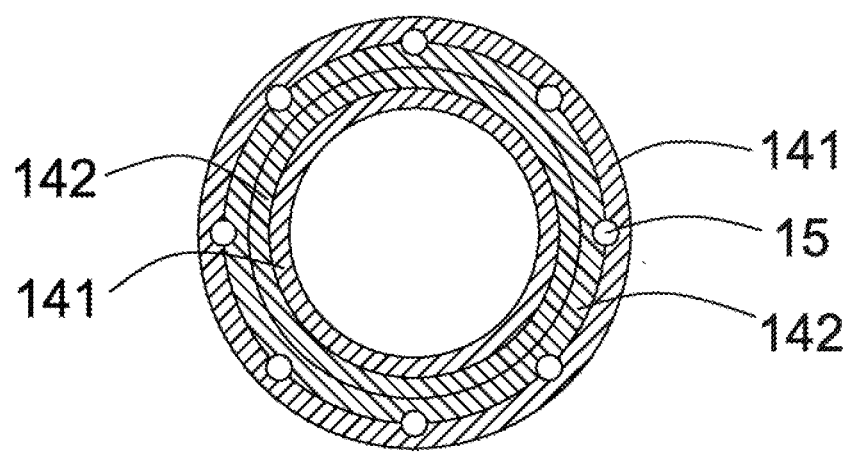
FIG. 2 is a sectional view along the direction A-A in FIG. 1.

As shown in FIG. 2, two ends of the first coating membrane 141 and the second coating membrane 142 are folded inwards (namely inside the lumen of the covered stent) and are connected with the second coating membrane 142 through the stent main body 15 so as to cover the proximal-end end surface 11 and the distal-end end surface 12 of the covered stent 10.

The present application further provides a manufacturing method of the above-mentioned covered stent 10, including that:

S1, an outer surface 131 of a stent main body 15 is covered with a first coating membrane 141, and an inner surface 132 is covered with a second coating membrane 142;

S2, the covered stent 10 covered with the above-mentioned coating membranes is thermally treated so as to adhere the first coating membrane 141 and the second coating membrane 142;

S3, after the coating membranes are cooled, two ends of the first coating membrane 141 and the second coating membrane 142 are cut to required lengths;

S4, the two ends of the first coating membrane 141 and the second coating membrane 142 are folded towards the inner surface 132; and S5, the first coating membrane 141 and the second coating membrane 142 which are folded towards the inner surface 132 are thermally treated so as to adhere the folded coating membranes with the second coating membrane 142. The first coating membrane 141 and the second coating membrane 142 may be ironed into a whole by using soldering iron after being folded inwards, or the covered stent 10 may be thermally treated again by using a thermal treatment furnace after the first coating membrane 141 and the second coating membrane 142 are folded inwards.

The prevent application may prevent blood flow from directly impacting the coating membranes on the proximal-end end surface and the distal-end end surface by a flanging design for the coating membranes covering the peripheral surface of the covered stent on the proximal-end end surface and the distal-end end surface of the covered stent, thereby avoiding tearing of the coating membranes on the inner and outer surfaces caused by long-term blood flow impact and a series of adverse effects caused by the tearing of the coating membranes.

Second Embodiment

Figure 3:
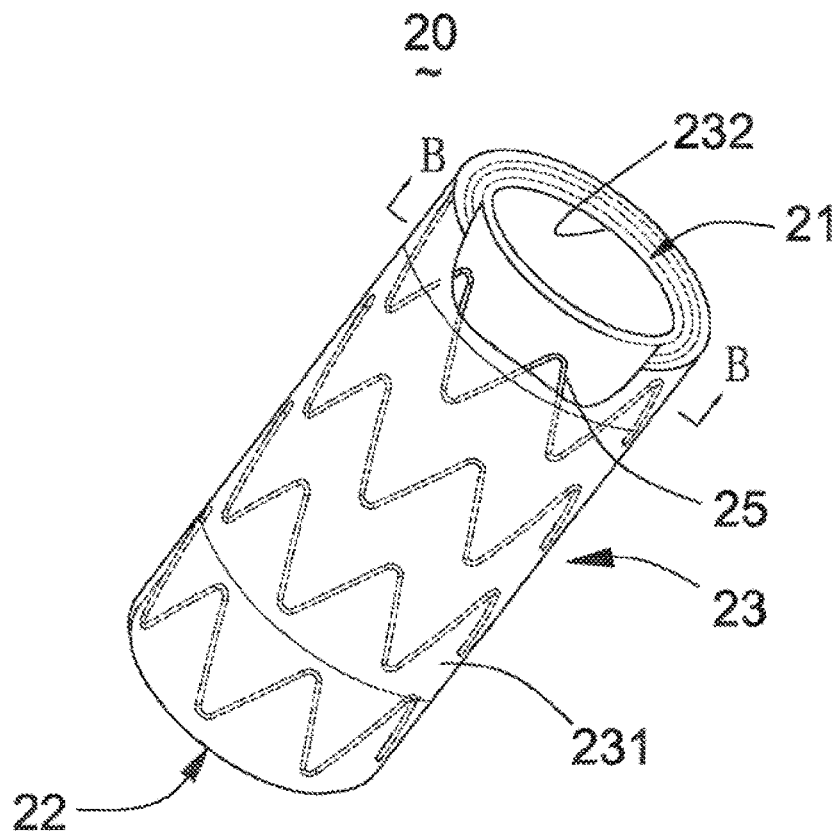
FIG. 3 is a structural schematic diagram of a second embodiment of a covered stent of the present application.
Figure 4:
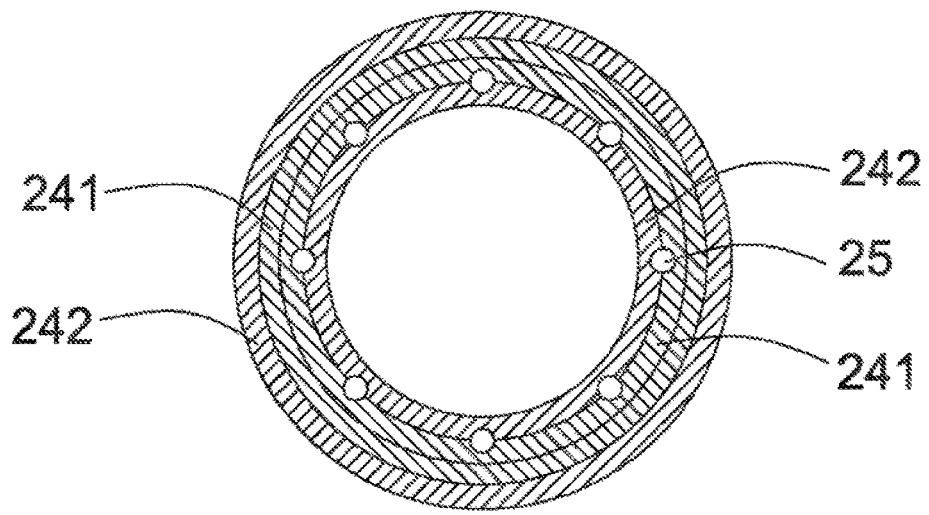
FIG. 4 is a sectional view along the direction B-B in FIG. 3.

As shown in FIG. 3, a covered stent 20 is of a tubular structure (used for forming a blood flow channel) with openings in two ends, and has a proximal-end end surface 21, a distal-end end surface 22 and a peripheral surface 23 located between the proximal-end end surface 21 and the distal-end end surface 22. The peripheral surface 23 includes an outer surface 231 and an inner surface 232 opposite to the outer surface 231. In the present embodiment, the outer surface 231 is covered with a first coating membrane 241, and the inner surface 232 is covered with a second coating membrane 242. The first coating membrane 241 and the second coating membrane 242 have certain thicknesses and are generally made of a biocompatible macromolecular material, such as a PET membrane or PTFE membrane. A stent main body 25 is arranged between the first coating membrane 241 and the second coating membrane 242. The first coating membrane 241 and the second coating membrane 242 are adhered by thermal treatment so as to clamp the stent main body 25 therebetween. The stent main body 25 is cut and expanded from a biocompatible plastic expansion material tubular product known in the art, and the tubular product may be medical stainless steel, or a cobalt-nobelium alloy, or a self-expansion material such as a nickel-titanium alloy. When made of a plastic expansion material, the stent main body 25 may be radially compressed in a delivery sheath tube and may be expanded to an initial shape and size through an inflatable balloon or an equivalent expansion mechanism. When made of the self-expansion material, the stent main body 25 may be radially compressed in the delivery sheath tube and recovers the initial shape and size in the absence of the compression of the delivery sheath tube. The stent main body 25 may be cut from the tube product or woven by a metal wire. As shown in FIG. 4, two ends of the first coating membrane 241 and the second coating membrane 242 are folded outwards (namely outside the lumen of the covered stent) and are connected with the first coating membrane 241 through the stent main body 25 so as to cover the proximal-end end surface 21 and the distal-end end surface 22 of the covered stent 20.

The present application further provides a manufacturing method of the above-mentioned covered stent 20, including that:

S1, an outer surface 231 of a stent main body 25 is covered with a first coating membrane 241, and an inner surface 232 is covered with a second coating membrane 242;

S2, the covered stent 20 covered with the above-mentioned coating membranes is thermally treated so as to adhere the first coating membrane 241 and the second coating membrane 242;

S3, after the coating membranes are cooled, two ends of the first coating membrane 241 and the second coating membrane 242 are cut to required lengths;

S4, the two ends of the first coating membrane 241 and the second coating membrane 242 are folded towards the outer surface 231; and S5, the first coating membrane 241 and the second coating membrane 242 which are folded towards the outer surface 231 are thermally treated so as to adhere the folded coating membranes with the first coating membrane 241. The first coating membrane 241 and the second coating membrane 242 may be ironed into a whole by using soldering iron after being overall inwards folded, or the covered stent 20 may be thermally treated again by using a thermal treatment furnace after the first coating membrane 241 and the second coating membrane 242 are folded inwards.

Third Embodiment

Figure 5:
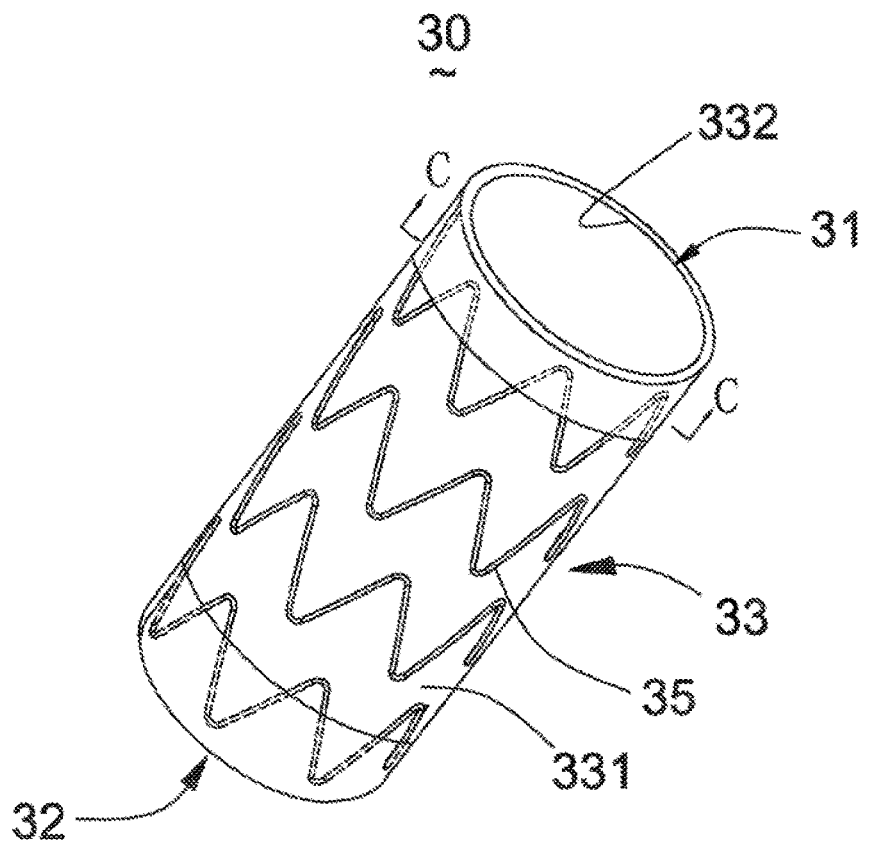
FIG. 5 is a structural schematic diagram of a covered stent of a third embodiment of the present invention, in which only the inner surface of a stent main body is covered with a second coating membrane.
Figure 6:
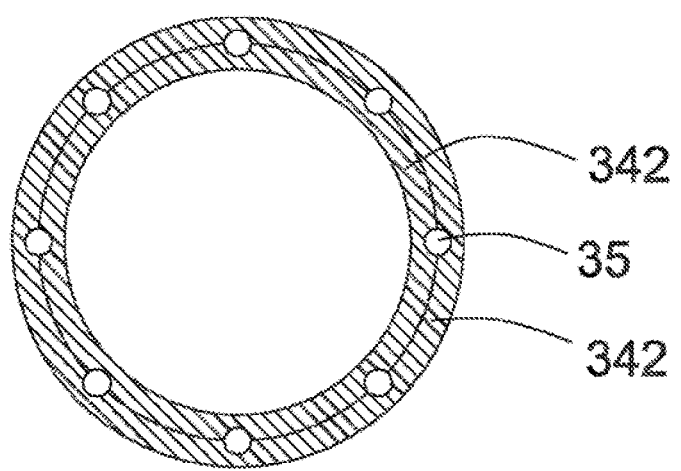
FIG. 6 is a sectional view along the direction C-C in FIG. 5.
Figure 7:
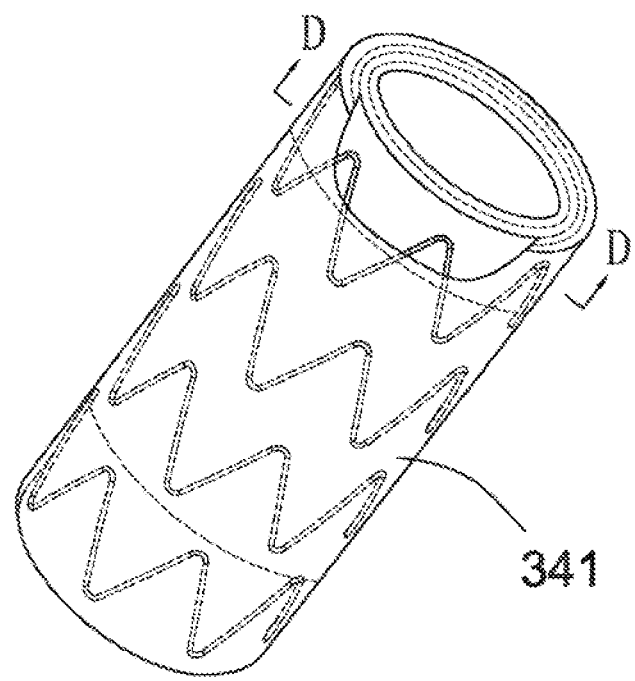
FIG. 7 is a structural schematic diagram of the covered stent of the third embodiment of the present invention, in which both the inner and outer surfaces of the stent main body are covered with coating membranes.
Figure 8:
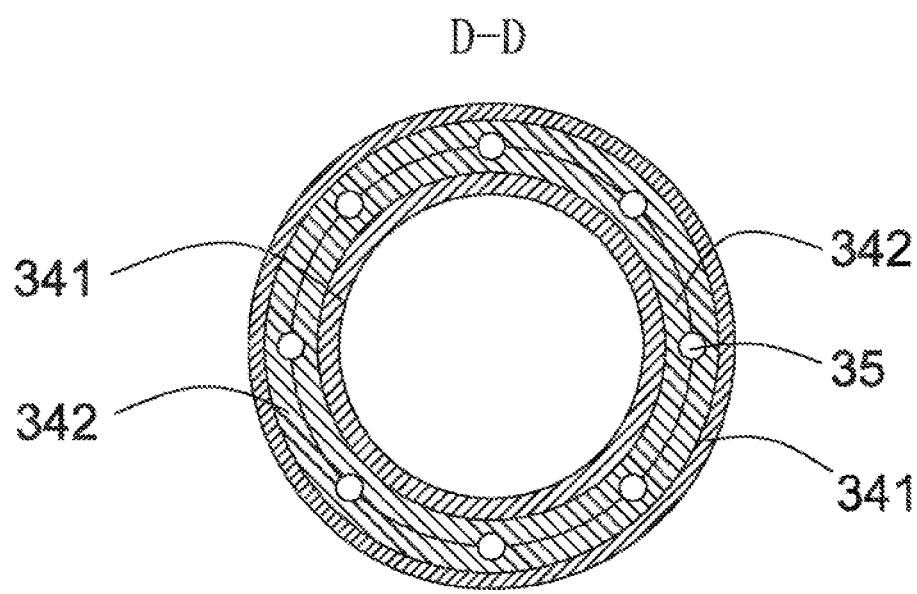
FIG. 8 is a sectional view along the direction D-D in FIG. 7.

As shown in FIG. 5, a covered stent 30 is of a tubular structure (used for forming a blood flow channel) with openings in two ends, and has a proximal-end end surface 31, a distal-end end surface 32 and a peripheral surface 33 located between the proximal-end end surface 31 and the distal-end end surface 32. The peripheral surface 33 includes an outer surface 331 and an inner surface 332 opposite to the outer surface 331. The inner surface 332 is covered with a second coating membrane 342. As shown in FIG. 6, two ends of the second coating membrane 342 are folded outwards (namely towards the outside of the lumen of the covered stent 30). As shown in FIG. 7, the outer surface 331 is covered with a first coating membrane 341. As shown in FIG. 8, two ends of the first coating membrane 341 are folded inwards (namely towards the inside of the lumen of the covered stent 30). A stent main body 35 is also arranged between the first coating membrane 341 and the second coating membrane 342. The first coating membrane 341 and the second coating membrane 342 are adhered by thermal treatment so as to clamp the stent main body 35 therebetween.

The present application further provides a manufacturing method of the above-mentioned covered stent 30, including that:

S1, an inner surface 332 is covered with a second coating membrane 342, and two ends of the second coating membrane 342 are cut to required lengths;

S2, the two ends of the second coating membrane 342 are folded towards an outer surface 331;

S3, the covered stent in Step S2 is thermally treated so as to allow the two ends of the second coating membrane 342 to be adhered with the second coating membrane 342 through a gap of a stent main body 35;

S4, an outer surface 331 is covered with a first coating membrane 341, and two ends of the first coating membrane 341 are cut to required lengths;

S5, the two ends of the first coating membrane 341 are folded towards the inner surface 332; and S6, the covered stent 30 in Step S5 is thermally treated so as to allow the two ends of the first coating membrane 341 to be adhered with the second coating membrane 342.

The above-mentioned embodiments are merely expressive of several implementation modes of the present application, and their descriptions are relatively specific and detailed, but are not to be interpreted as limitations to the scope of the patent for invention. It should be noted that persons of ordinary skill in the art can further make a any number of changes and improvements without departing from the scope of the present application, and these changes and improvements shall all fall within the protection scope of the present application. Therefore, the protection scope of the patent of the present application shall be based on attached claims.

The invention claimed is:

1. A covered stent, comprising: a proximal-end end surface, a distal-end end surface and a peripheral surface located between the proximal-end end surface and the distal-end end surface, the peripheral surface comprising an inner surface and an outer surface opposite to the inner surface; the outer surface is covered with a first coating membrane, and the inner surface is covered with a second coating membrane; the covered stent further comprising a stent main body arranged between the first coating membrane and the second coating membrane; and the two ends of the second coating membrane are folded towards the outer surface and are connected with the second coating membrane through the stent main body and the two ends of the first coating membrane are folded towards the inner surface and are connected with the second coating membrane.

2. A membrane covering method of the covered stent according to claim 1, comprising:

S1, covering the outer surface of the covered stent with a first coating membrane, and covering the inner surface with a second coating membrane;

S2, thermally treating the covered stent covered with the coating membranes so as to adhere the first coating membrane and the second coating membrane;

S3, after the coating membranes are cooled, cutting two ends of the first coating membrane and the second coating membrane to required lengths;

S4, folding the two ends of the first coating membrane towards the inner surface and the second coating membrane towards the outer surface; and S5, thermally treating the first coating membrane which is folded towards the inner surface and the second coating membrane which is folded towards the outer surface so as to adhere the folded coating membranes with the second coating membrane.

3. The covered stent according to claim 1, wherein the first coating membrane and the second coating membrane are made of a PET membrane or PTFE membrane.

4. The covered stent according to claim 1, wherein the stent main body is cut and expanded from a biocompatible plastic expansion material tubular.

* * * * *